(12) United States Patent
Annergren et al.

(10) Patent No.: US 6,383,609 B1
(45) Date of Patent: May 7, 2002

(54) ABSORBENT STRUCTURE COMPRISING A HIGHLY ABSORBENT POLYMER, AND AN ABSORBENT ARTICLE COMPRISING THE ABSORBENT STRUCTURE

(75) Inventors: Jeanette Annergren, Mölnlycke; Petter Bragd; Gunilla Himmelmann, both of Göteborg, all of (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 09/445,596

(22) PCT Filed: Jun. 24, 1997

(86) PCT No.: PCT/SE97/01127

§ 371 Date: Apr. 11, 2000

§ 102(e) Date: Apr. 11, 2000

(87) PCT Pub. No.: WO98/58687

PCT Pub. Date: Dec. 30, 1998

(51) Int. Cl.$^7$ ................................................. B32B 1/00
(52) U.S. Cl. ...................... 428/178; 428/70; 428/297.4; 428/71

(58) Field of Search ................................. 428/297.4, 70, 428/71, 76, 158, 178, 36.5; 502/402, 439; 264/235

(56) References Cited

U.S. PATENT DOCUMENTS

| | | | | |
|---|---|---|---|---|
| 4,444,922 A | * | 4/1984 | Gutowski et al. | 523/339 |
| 4,782,097 A | * | 11/1988 | Jain et al. | 521/56 |
| 4,917,845 A | * | 4/1990 | Cohn | 264/109 |
| 5,126,382 A | * | 6/1992 | Hollenberg | 524/56 |
| 5,328,935 A | * | 7/1994 | Van Phan et al. | 521/64 |
| 5,573,994 A | * | 11/1996 | Kabra et al. | 502/402 |

FOREIGN PATENT DOCUMENTS

WO 95/31500 11/1995

* cited by examiner

*Primary Examiner*—Merrick Dixon
(74) *Attorney, Agent, or Firm*—Burns, Doane, Swecker & Mathis, L.L.P.

(57) ABSTRACT

An absorbent article comprising a polysaccharide-based highly absorbent material, which is produced by desiccating a cross-linked hydrogel using a polar solvent.

11 Claims, 10 Drawing Sheets

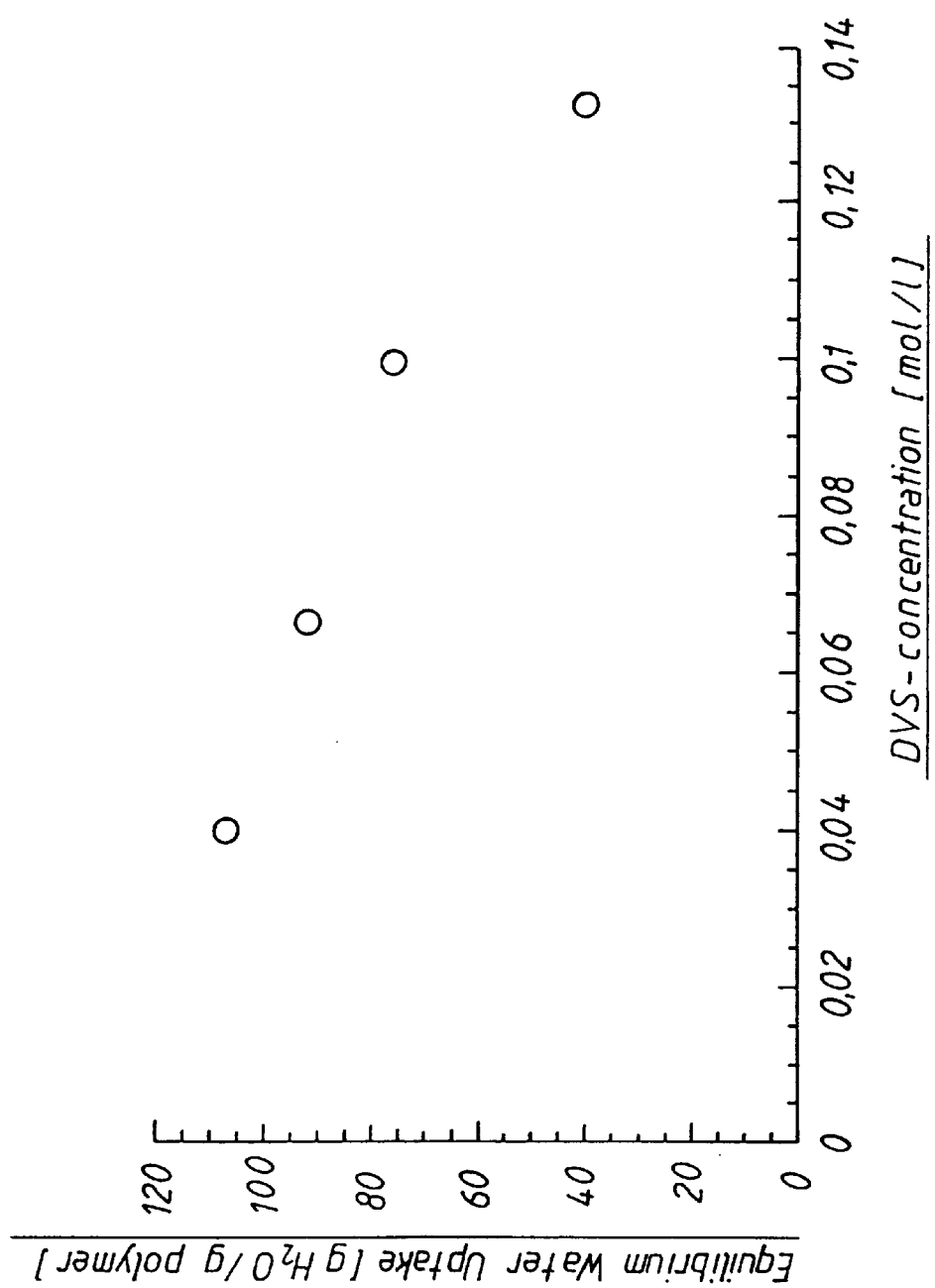
DIAGRAM 1

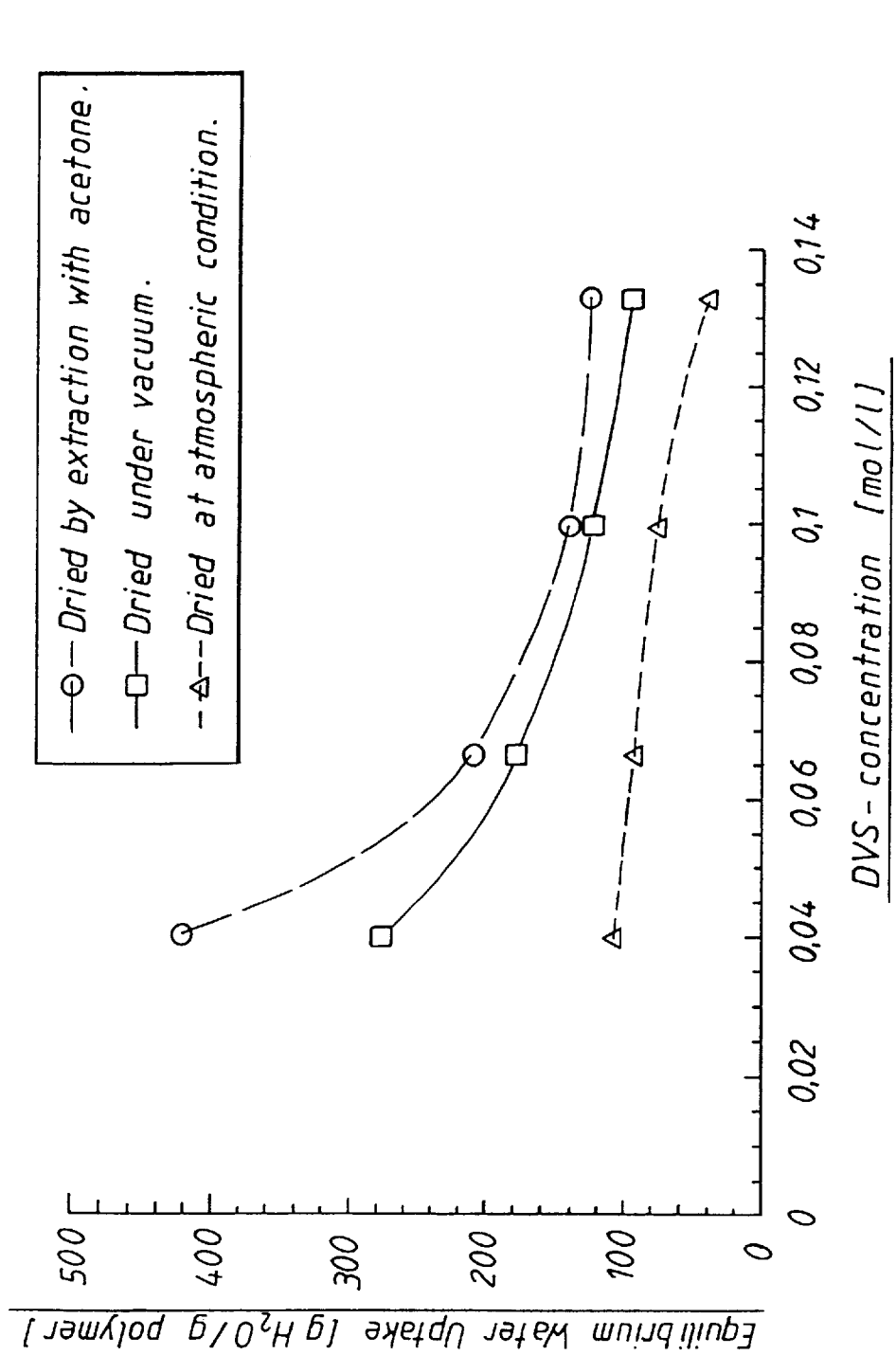
DIAGRAM 2

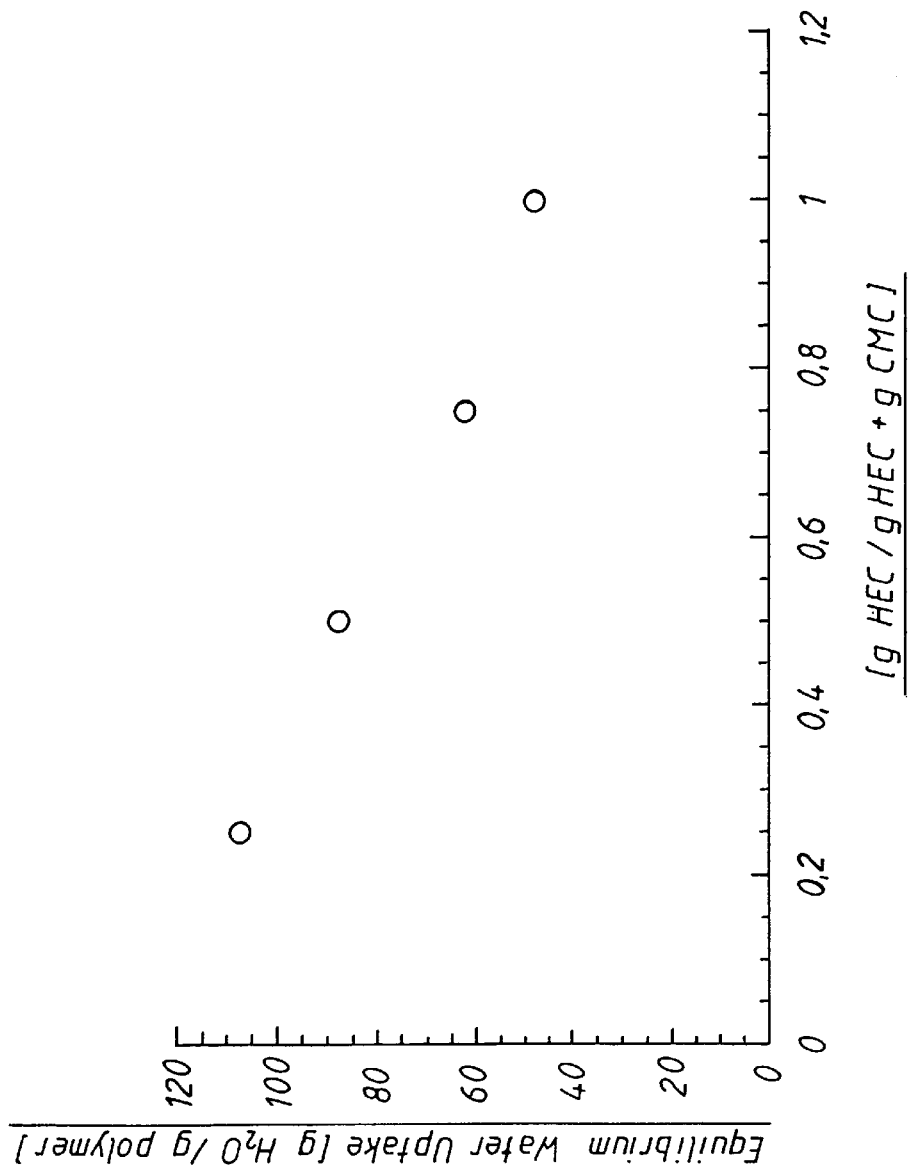

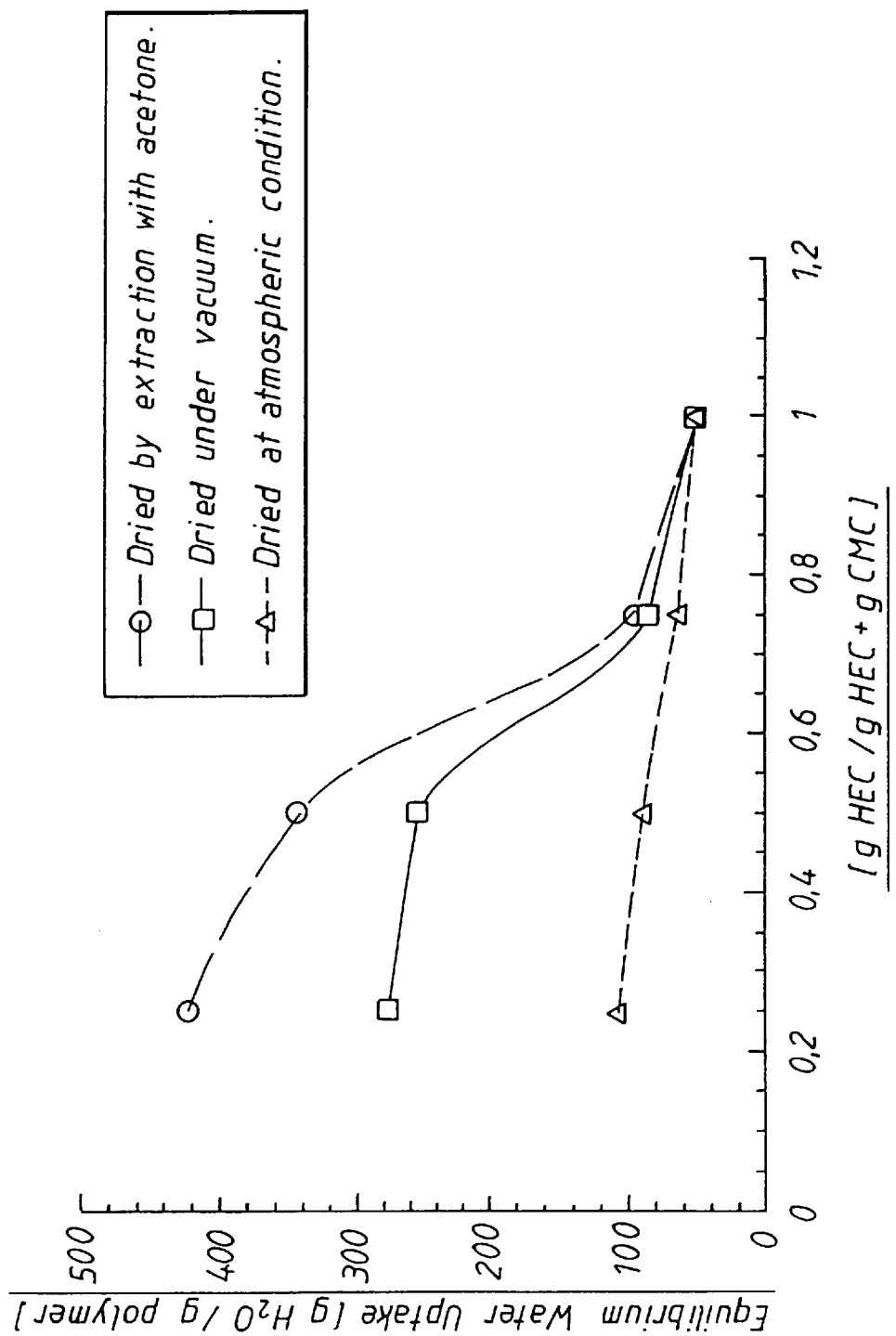

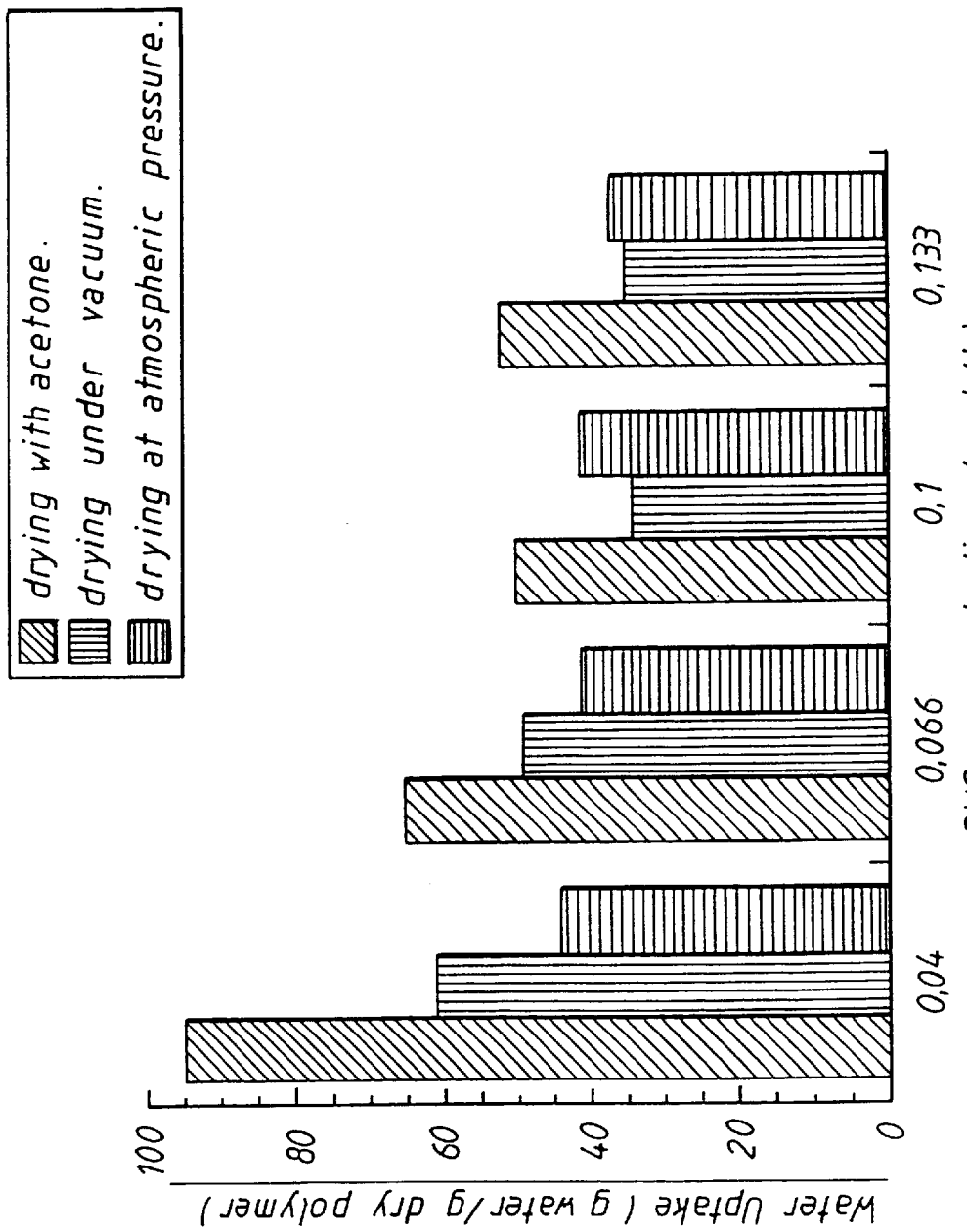

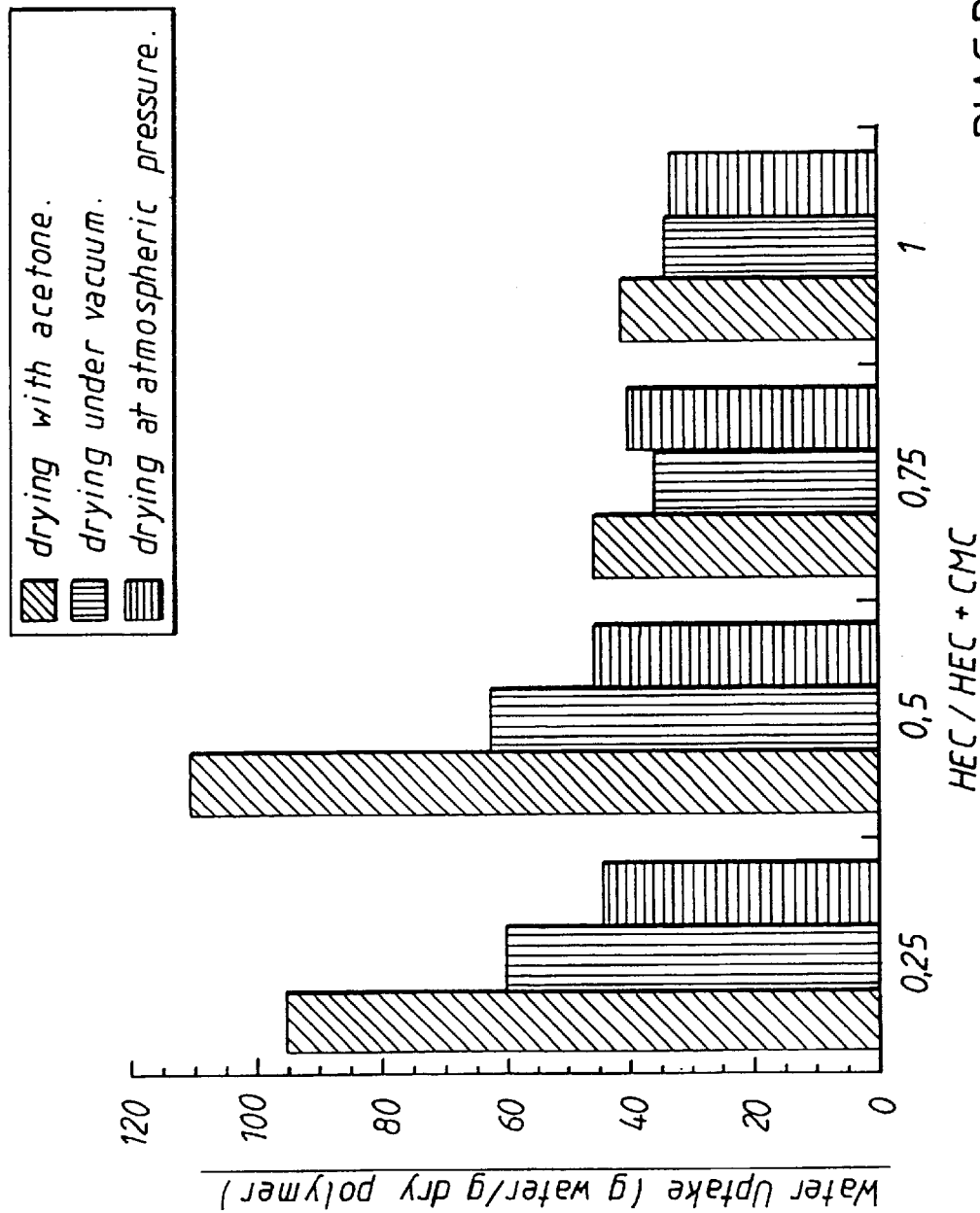

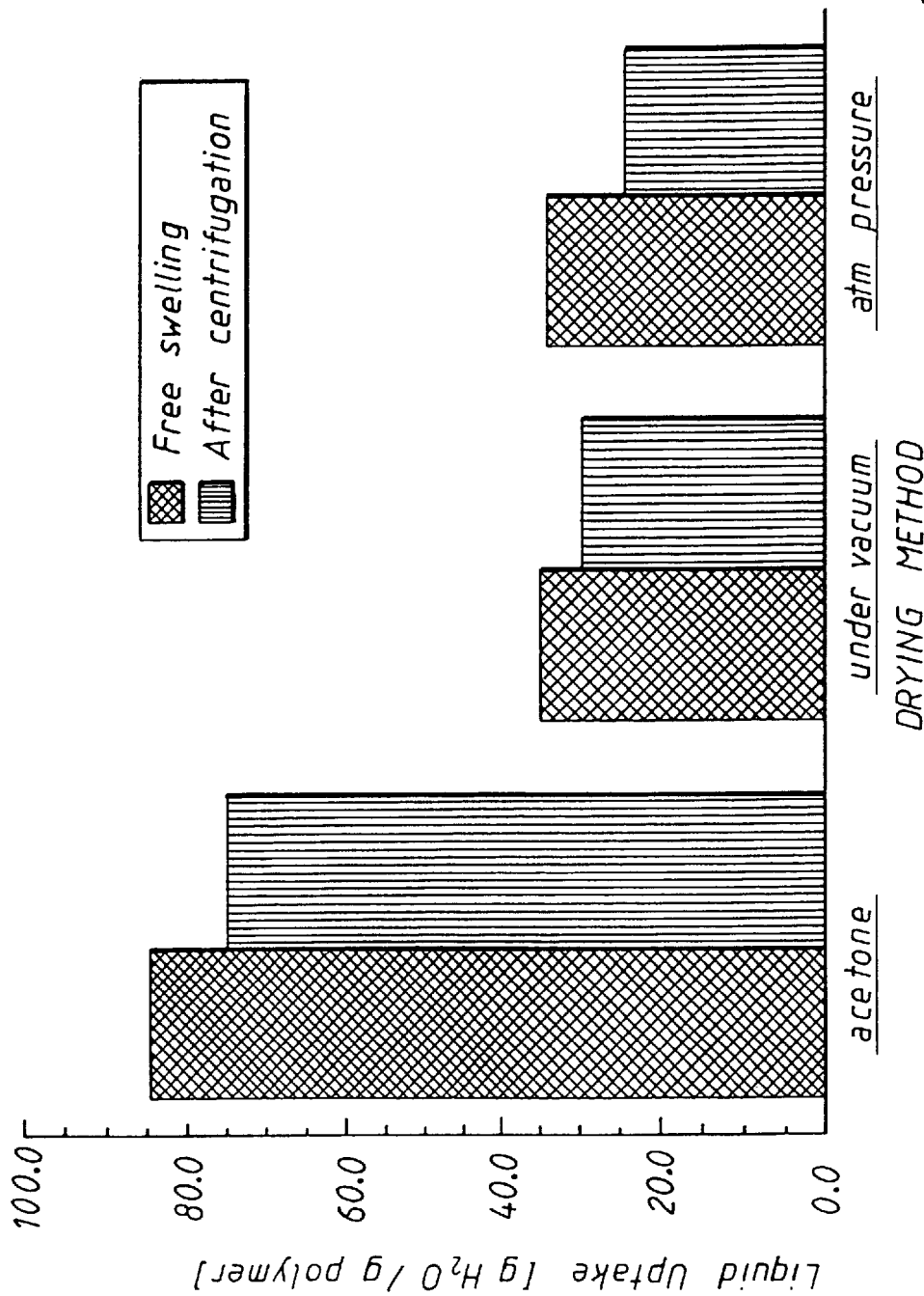
DIAGRAM 7

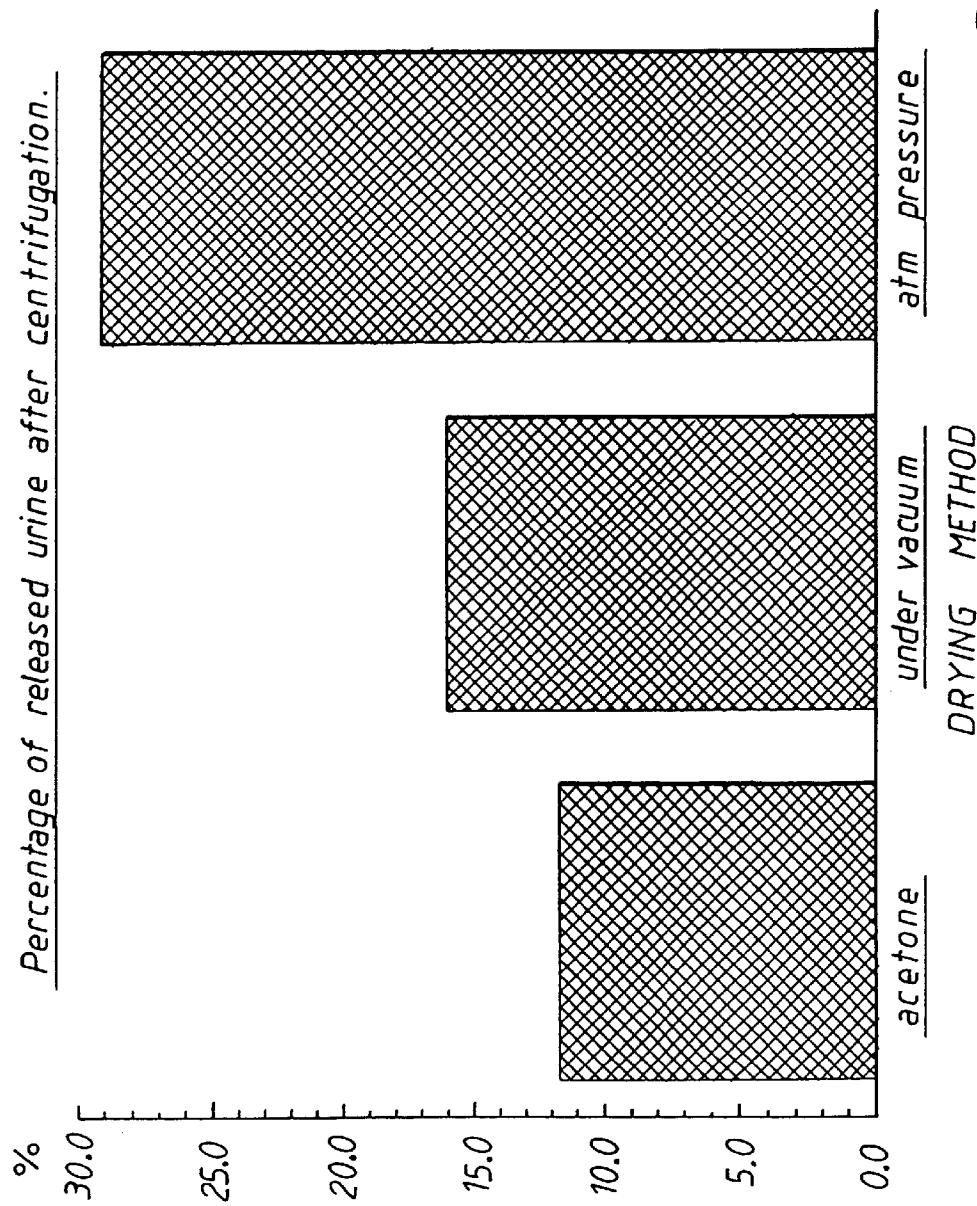

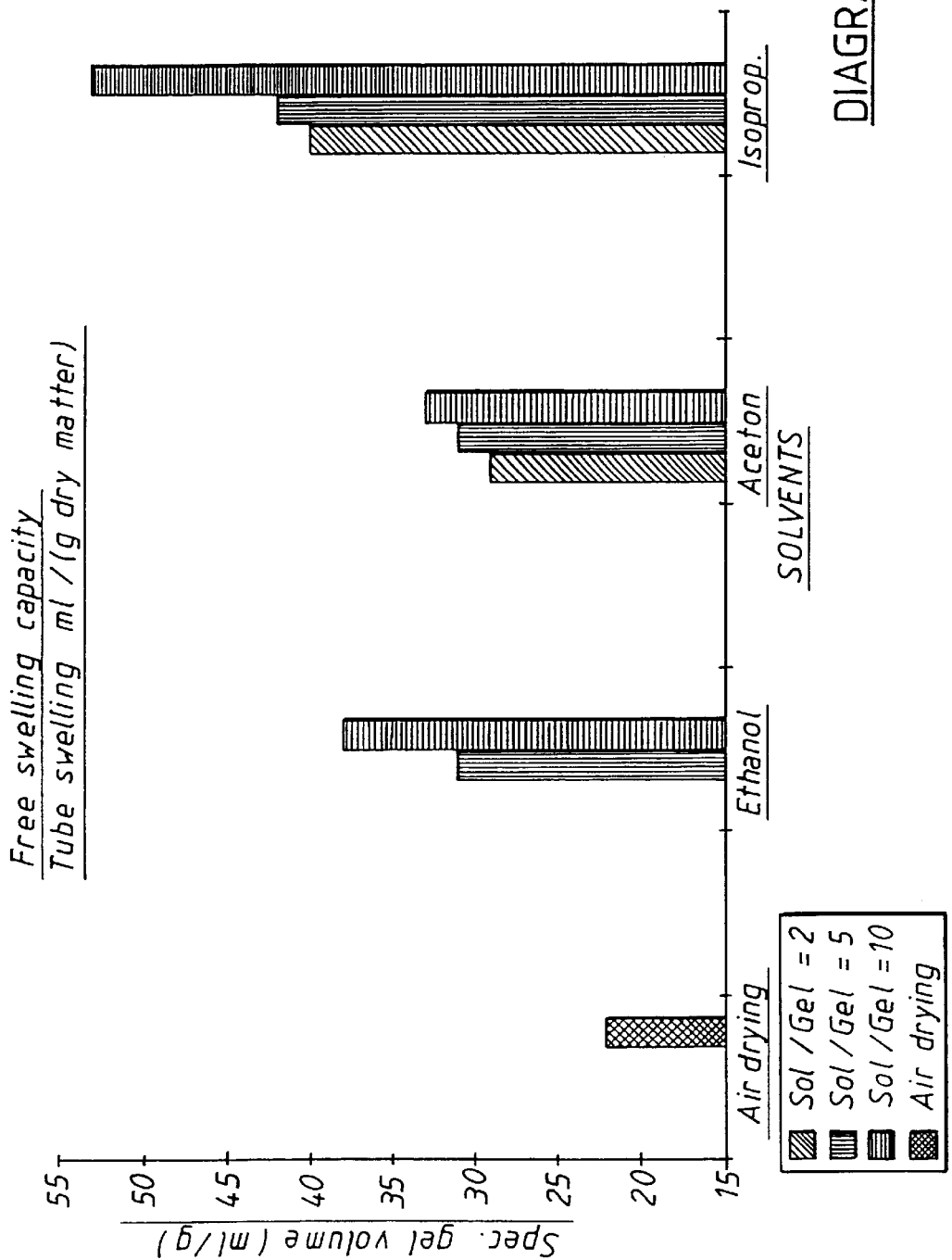

ABSORBENT STRUCTURE COMPRISING A HIGHLY ABSORBENT POLYMER, AND AN ABSORBENT ARTICLE COMPRISING THE ABSORBENT STRUCTURE

TECHNICAL FIELD

The invention pertains to an absorbent structure comprising a polysaccharide-based highly absorbent material.

The invention also relates to an absorbent article, such as a diaper, an incontinence protector, a sanitary napkin, or the like, comprising the absorbent structure.

BACKGROUND OF THE INVENTION

For many applications, such as in absorbent articles intended for absorption of body fluids, it has become increasingly common to use what are known as superabsorbent materials. With superabsorbent materials are meant polymers which are capable of absorbing liquid in amounts corresponding to several times the weight of the polymer and which upon absorption form a water-containing gel.

The main advantage of using superabsorbent materials in absorbent articles is that the volume of the absorbent articles can be considerably reduced in comparison to the volume of absorbent articles mainly formed from absorbent fibrous materials such as fluffed cellulose pulp, or the like. Another advantage is that superabsorbents, when compared to fibrous absorbents such as, for instance, fluffed cellulose pulp, have a higher capability of retaining liquid under pressure. Such a property is, for instance, advantageous when the absorption material is used in diapers, incontinence guards or sanitary napkins, since absorbed body fluid is retained in the absorbent article and is not squeezed out of the article, for instance when the user is sitting down.

However, a disadvantage with many of the superabsorbent materials presently being used in absorbent articles such as diapers, incontinence protectors or sanitary napkins, is that they are not produced from renewable raw materials. In order to solve this problem, it has been suggested that superabsorbents based on different types of renewable starting materials, such as polysaccharides and, in particular, starch, be used. Unfortunately, the polysaccharide-based superabsorbents which have so far been produced exhibit considerably lower absorption capacity than the commonly used polyacrylate-based superabsorbents. Further, the ability of the polysaccharide-based superabsorbents to retain absorbed liquid when the superabsorbent is subjected to load is low in comparison with polyacrylate-based superabsorbents.

In WO 95/31500, a method for producing absorbent, preferably superabsorbent, foam materials by phase separation and crosslinking of a polymer solution is described. The absorbent materials obtained exist in the form of a crosslinked open-celled polymer foam, which implies that fluid may pass between cells. By means of the described production method, it is also said to be possible to obtain biodegradeable absorbent foam materials. Preferred polymers for producing the absorbent materials which are disclosed in WO 95/31500 are hydroxyethyl cellulose (HEC) and hydroxypropyl cellulose (HPC), which are preferably crosslinked with divinyl sulphone (DVS).

The known absorbent foam materials are relatively expensive to produce and are primarily intended for medical applications, such as controlled release systems or as artificial skin and blood vessels. However, a further possible use for the described foam materials is said to be in reusable diapers or the like. The high production cost does, however, mean that the known foam materials would, in practice, not be contemplated as absorption material for absorbent articles intended for single use only.

For these reasons, there exists a demand for an improved superabsorbent material based on renewable raw materials. Accordingly, the absorption capacity for polysaccharide-based superabsorbents needs to be improved in order to make such superabsorbents an equal alternative with regard to absorbency and when compared to the superabsorbents which are commonly used today. Moreover, there exists a need for a disposable absorbent article comprising an absorbent structure with a superabsorbent material which may be produced using low-cost, readily available, renewable starting materials.

DESCRIPTION OF THE INVENTION

The present invention provides an absorbent structure of the kind mentioned in the introduction, and having an improved absorption capacity as compared to previously known such absorbent structures.

The absorbent structure in accordance with the invention is primarily distinguished by highly absorbent material being produced by crosslinking and desiccation of a liquid solution containing a starting material in the form of a crosslinkable polysaccharide-based polymer, wherein the starting material, after the crosslinking reaction, exists in the form of a liquid-swollen hydrogel, and wherein the crosslinked, liquid-swollen hydrogel is desiccated by extraction with a polar solvent.

A wide range of solvents may be used for the initial solution containing the polysaccharide-based polymer starting material. However, the solution containing the starting material is preferably an aqueous solution.

Surprisingly, it has been shown that by drying a crosslinked polysaccharide using a polar solvent, such as ethanol, acetone or isopropanol, a superabsorbent material can be obtained exhibiting superior absorbency when compared to a material of the same composition but dried using another method. The improved absorbency is evident both in a higher absorption capacity and in a greater ability to retain absorbed liquid even when the absorption material is subjected to pressure. The absorbency of a superabsorbent material which has been dried using a polar solvent is considerably higher than that of a corresponding superabsorbent material which has been dried using any other method, regardless of whether the absorbed liquid is water or a salt-containing solution such as urine.

When comparing electron scanning micrographs of crosslinked superabsorbent gels with the same composition, but dried in different ways, it is clearly evident that the microstructure of the dried gels, or xero-gels, show significant differences depending on the method of desiccation. Accordingly, an air-dried gel exhibits a dense, compact structure, while a gel which has been dried by solvent extraction exhibits a structure with a high degree of microporosity. Vacuum drying produces a structure exhibiting some degree of microporosity and can be said to represent a form between the Structure obtained by air-drying and the structure obtained by the solvent drying in accordance with the invention.

A probable explanation of the advantageous effect of solvent drying is that a commonly occurring phenomenon producing a dense, horny, non-absorbing structure, is avoided. This phenomenon is well known to the person skilled in the art, even though its exact mechanisms have not yet been fully explained. However, the effect is that the crosslinked gel exhibits reduced swelling capability and, thus, reduced absorption capacity. Accordingly, in comparison with conventionally dried gels, a gel which has been dried using a polar solvent exhibits a more open and flexible structure, something that affects the absorption process in a positive way.

The solvent-dried superabsorbent polymer exists in the form of a microporous gel. The superior absorption properties exhibited by the gel are believed to be the result of liquid partly being bound in the gel in a conventional manner and partly being absorbed in the microvoids in the gel. When the gel absorbs liquid, the gel swells, whereby the size of the microvoids increases and the absorption capacity of the gel is enhanced.

The starting material may comprise a polymer blend comprising an electrically charged polysaccharide-based polymer and an electrically uncharged polysaccharide-based polymer. The ratio between the charged polymer and the uncharged polymer is preferably between about 2:1 and about 4:1 and most preferably about 3:1.

A major advantage afforded by the invention is that carboxymethyl cellulose (CMC) can be used as a starting material for the production of a superabsorbent material displaying high absorption capacity and good liquid retention. The fact that CMC is produced from wood which is a renewable material source and, further, that it is readily available and comparatively low in cost, makes CMC particularly suitable for use in disposable absorbent articles. Moreover, with regard to biodegradability and compostability, CMC exhibits excellent characteristics.

However, it has been found to be less suitable to use CMC as sole starting material for the production of a superabsorbent material, since CMC tends to form intramolecular crosslinks instead of crosslinks between different molecules. An absorption material having particularly good properties may thus be obtained with a starting material comprising a mixture of CMC in the form of its sodium salt (CMCNa) and hydroxyethyl cellulose (HEC). A suitable proportion between the amount of CMCNa and HEC has thereby been found to be between about 2:1 and about 4:1 and preferably about 3:1. At a lower concentration of HEC, the resulting cross-linked gel does not exhibit sufficient gel strength. High concentrations of HEC should be avoided since the swelling capacity and, accordingly, the absorption capacity will be insufficient if the HEC concentration is too high.

Alternatively, it is possible to use combinations of other charged and uncharged polysaccharides. Some further examples of suitable charged polysaccharides are carboxymethyl starch, oxidized starch and oxidized cellulose. Suitable uncharged polysaccharides include, but are not limited to: ethylhydroxyethyl cellulose (EHEC), hydroxypropyl cellulose (HPC) and hydroxypropyl starch (HPS).

It is further possible to use pectin as starting material.

The polymer solution is preferably crosslinked with a crosslinking agent producing covalent crosslinks. Some examples of crosslinking agents of this kind are divinylsulphone (DVS), acetaldehyde, formaldehyde, glutaraldehyde, diglycidyl ether, diisocyanates, dimethyl urea, epichlorohydrin, oxalic acid, phosphoryl chloride, trimetaphosphate, trimethylomelamine, polyacrolein. Naturally, it is also possible to use ionic crosslinking or physical crosslinking such as hydrophobic/hydrophilic interactions, or the like.

A superabsorbent material of the above-described kind may be readily combined with fibres and can accordingly be mixed with absorbent fibres such as fluffed cellulose pulp, rayon, peat moss, cotton, hemp, flax, or the like, using any conventional method. Furthermore, the highly absorbent material may be mixed with non-absorbent fibres such as polyethylene, polypropylene, polyester, nylon, bicomponent fibres, or the like. Clearly, it is possible to mix different types of fibres in an absorbent fibrous structure in order to achieve an optimal combination of characteristics such as absorbency, liquid retention, shape stability, and resiliency. The fibrous structure may be bonded, for instance by the melting of thermoplastic fibres comprised in the fibrous structure, or by adding a special binding agent. In addition, the fibrous structure may have been subjected to further processing, such as compression, needling, softening, or the like.

The highly absorbent material may, of course, alternatively be placed in a layer in an absorbent body comprising further layers of fibres, nonwoven sheets, tissue paper, or the like. The highly absorbent material may be a self-sustaining layer, or may be applied onto or within a substrate. Some examples of materials which may serve as substrates are tissue sheets, foam materials, nonwoven sheets, fibrous webs, structures having pockets in which the highly absorbent material is arranged, or the like.

BRIEF DESCRIPTION OF DIAGRAMS AND FIGURES

The invention will be described in greater detail in the following, by way of example only, and with reference to the Diagrams and Figures shown in the attached drawings, wherein:

Diagr. 1 shows the water uptake capability for air-dried gels produced with different amounts of DVS;

Diagr. 2 shows the water uptake capability for gels dried using different methods and with different addition of DVS;

Diagr. 3 shows the water uptake capability for air-dried gels with different concentration of HEC;

Diagr. 4 shows the water uptake capability for gels dried using different methods and with different concentration of HEC;

Diagr. 5 shows the water uptake capability in synthetic urine (SUR) for gels dried using different methods and with different DVS concentrations;

Diagr. 6 shows the water uptake capability in synthetic urine for gels dried using different methods and with different relation in the mixture of CMCNa/HEC;

Diagr. 7 shows the retention of synthetic urine for gels dried using different methods;

Diagr. 8 shows the percentage of liquid which is released upon centrifugation of hydrogels dried using different methods; and Diag. 9 shows the swelling capacity for a pectin-based absorption material after drying with different solvents.

Additionally:

FIG. 1 shows a diaper having an absorption body comprising solvent-dried, highly absorbent material;

FIG. 2 shows a cross-section taken along line II—II through the diaper in FIG. 1.

DESCRIPTION OF METHODS

Gel Preparation

The hydrogels which were used in the following examples, were obtained by crosslinking mixtures of CMCNa and HEC, using DVS as crosslinking agent. The reason for choosing DVS as crosslinking agent is that DVS provides a reliable and reproducible crosslinking result. Thus, DVS is well suited for the production of crosslinked materials for use in comparative work. However, the invention shall not in any way be regarded as being restricted to the use of DVS as crosslinking agent. Accordingly, and as mentioned above, any suitable crosslinking agent or crosslinking method may be used.

The crosslinking reaction was performed in an alkaline aqueous solution with 0.02 M potassium hydroxide (KOH) at 20° C. CMCNa and HEC were dissolved in distilled water-containing the desired amount of DVS. After thorough mixing for 24 hours, potassium hydroxide was added, thereby starting the crosslinking reaction. All reactions were performed with a reaction solution having an overall polymer concentration equal to 2% by weight.

After 24 hours, the crosslinked hydrogel was soaked in distilled water in order to reach equilibrium water sorption. The water surrounding the hydrogel was renewed at least three times. Each time, an amount of water corresponding to 5 times the weight of the hydrogel measured immediately after the crosslinking reaction was used. The soaking procedure was terminated after 36–48 hours. Subsequently, the swelled hydrogel was removed from the water and desiccated.

Desiccation Methods

Three different methods of desiccation were used:
i) air drying at atmospheric pressure
ii) drying under vacuum
iii) drying by extraction with a polar solvent Air drying consisted simply in leaving the swollen hydrogel under room conditions (25° C. and 50% relative humidity) until completely dry.

Vacuum drying was performed by placing swollen hydrogels in a container connected to a vacuum pump and kept at a pressure equal to 0.01 Torr.

Drying by extraction with a solvent consisted in placing water swollen hydrogels in the solvent at room temperature and with gentle mixing. The solvent was replaced two times and the amount of solvent used each time was approximately twice that of the swollen hydrogel. The reason why acetone was used in all examples in which the gels were crosslinked with DVS is that, in contrast to the alcohols, acetone will not react with DVS. However, if crosslinking is carried out in an alternative manner, such as, for instance, enzymatically or with radiation, a polar solvent such as ethanol or isopropanol may be used.

After desiccation, the dried gels produced by air drying and vacuum drying were ground in a laboratory grinder. In the solvent drying process, the stirring caused the gel to break into smaller pieces, which were directly used in Examples 1–3. All subsequent measurements were performed on desiccated gel which had been ground or broken up into smaller pieces.

Liquid Uptake Capacity

The liquid uptake capacity for fibrous structures containing superabsorbent material was determined by letting test bodies made from fluffed cellulose pulp having 20% by weight of a crosslinked, dried, and ground gel absorb liquid according to a principle commonly known as "demand wettability". The measurements were made with a GATS-like apparatus. The test bodies were allowed to absorb liquid from a communicating vessel. The amount of liquid in the vessel was continuously measured using scales. The test continued for 2 hours, whereafter the amount of liquid which had been absorbed by the test body was recorded. By knowing the water uptake capacity of the fluffed cellulose pulp, the amount of liquid absorbed by the crosslinked gel could subsequently be calculated.

Each measurement was the mean value of two recordings made with identical test bodies.

The test liquid was synthetic urine, SUR. The composition of the SUR was 60 mmol/l KCl, 130 mmol/l NaCl, 3.5 mmol/l $MgSO_4$, 2.0 mmol/l $CaSO_4.2H_2O$, 300 mmol/l urea, 1 q/l of a 0.1% solution of Triton X-100 which is a surfactant sold by Aldrich.

Free Swelling Capacity

Free swelling was determined using two different methods. Accordingly, in Examples 1–3, the ability of the gel to absorb liquid was measured according to a first method by immersing a piece of the gel in the test liquid and allowing the gel to absorb liquid until saturated. The gel was subsequently removed from the liquid and weighed.

In Example 4, the free swelling capacity on absorption was measured according to a second method by introducing 0.100 g±0.002 g crosslinked, dried gel in a test tube having dimensions 150 mm×16 mm. The test tube was provided with a screw cap and had a volume of 20 ml. The height of the dry, unswollen sample was measured with a millimetre stick and recorded. Thereafter, 15 ml synthetic urine (SUR) was added with an automatic pipette.

The sample was left to swell for 2 hours until equilibrium was reached, whereafter the height of the sample in the test tube was again measured and recorded.

From the thus obtained measurements, the change in volume/weight was calculated according to:

$$A(T) = \frac{(h(s) - h(t)) * \Pi * r^2}{m(t)}$$

where
$A(T)$=Absorptions capacity in g/cm$^3$
$h(s)$=height in millimetres for the swollen sample
$h(t)$=height in millimetres for the dry sample
$m(t)$=the dry weight in grams for the sample
$r$=the radius of the test tube in millimetres (0.72 mm)

DESCRIPTION OF EXAMPLES

Example 1

The water uptake capability was measured according to the free swelling method for different gels obtained by crosslinking an aqueous solution containing 2 percent by weight of a mixture of CMCNa and HEC, wherein the relation CMCNa:HEC=3:1, and with different amounts of crosslinking agent, divinylsulphone (DVS).

As can be seen in Diagr. 1, the swelling capability for a gel dried under room conditions (25° C., atmospheric pressure and 50% relative humidity) decreases with increasing content of DVS. The reason for this is that a higher degree of crosslinking increases the resistance to swelling of the gel. At a DVS-content below the lowest content of 0.04 mol/l given in Diagr. 1, the gel strength of the resulting gel is not sufficiently high for the gel to be useful in practice.

Diagr. 2 illustrates how different desiccation methods affect the water uptake capability for the xero-gels presented in Diagr. 1. As is clearly evident from Diagr. 2, the gel which has been dried by extraction with acetone has a higher water uptake capability than corresponding air-dried and vacuum-ried gels. This statement is true regardless of the DVS-content.

Example 2

The water uptake capability was measured for different gels obtained by crosslinking and drying of a CMCNa/HEC-mixture in an aqueous solution containing 2 percent by weight of the CMCNa/HEC-mixture and with 0.04 mol/l DVS as crosslinking agent and further at different mixing ratios for CMCNa:HEC.

Diagr. 3 shows how the water uptake capability for air-dried xero-gels decreases with increased content of HEC. The decrease in water uptake capability is partly due to the fact that the resistance to swelling of the gel is greater at a higher degree of crosslinking. By mixing CMCNa with HEC, it is possible to increase the gel strength of the crosslinked gel, since HEC has a positive effect on the formation of intermolecular crosslinks. When the HEC content is below 0.25, the gel strength of the crosslinked gel is too low for most practical applications.

A further explanation of the reduction in liquid uptake capability with increasing HEC content may be that the amount of fixed ionic charges present on the macromolecular chains is decreased when the HEC content is increased.

The curves shown in Diagr. 4 indicate that drying by extraction with acetone produces a significantly improved liquid uptake capability, as long as the HEC content does not exceed approximately 50% of the polymer blend.

Example 3

The liquid uptake capability for hydrogels dried using different methods were compared when the absorbed liquid was a solution of NaCl in water. The ionic strength of the solution was 0.15 mol/l.

It is clear from Diagr. 5 that acetone-dried hydrogel has a considerably higher uptake capability or swelling capacity than hydrogel which has been dried under vacuum or with air. The improved liquid uptake capability for acetone-dried hydrogel remains, as is evident from Diagr. 5, even if the DVS concentration is changed.

From Diagr. 6, it can be deduced that acetone-dried hydrogel exhibits a higher liquid uptake capability in synthetic urine when compared to air-dried or vacuum-dried hydrogel, regardless of the ratio between the amount of CMCNa and the amount of HEC.

In the tests presented in Diagrams 7 and 8, synthetic urine (SUR) was used instead of the NaCl solution used in Diagrams 5 and 6.

From Diagr. 7, it is evident that the liquid retention capacity of acetone-dried hydrogel is higher than for gels which have been dried in other ways. Accordingly, the ability to retain liquid upon centrifugation of the hydrogels is higher for the acetone-dried gel than for hydrogels which have been dried in air or under vacuum, both in absolute numbers and in relation to the liquid uptake capability of the gels at free swelling.

In Diagr. 8, it is shown that the portion of the synthetic urine which is extracted by centrifugation of a gel which has been allowed to swell freely in synthetic urine is smallest for acetone-dried gel and almost three times greater for air-dried gel.

Example 4

In Diagr. 9, it is shown how desiccation with different solvents affects the free swelling capacity of a crosslinked gel based on pectin, and how the relation in the mixture between the gel and the solvent affects the swelling capacity of the dried gel. The gel was crosslinked with an agent which could not react with alcohols, which means that, when using solvents such as ethanol and isopropanol, no reaction between the alcohols and the crosslinking agent occured.

The swelling capacity for an air-dried, pectin-based gel is shown as a reference. The measurements were carried out by leaving the samples to swell freely in a test tube as described in the second of the free swelling methods.

As is apparent from Diagr. 9, the swelling capacity for a gel which has been dried using isopropanol is better than for a gel which has been dried using ethanol or acetone. All solvent-dried gels exhibit a higher swelling capacity than an air-dried gel.

From Diagr. 9, it can further be seen that the relation between the amount of gel and the amount of solvent which is used in the drying process is important for the swelling capacity of the gel. Hence, the swelling capacity is higher for those gels in which a larger quantity of solvent was used, since, by using a larger quantity of solvent in the drying process, the water may be more fully extracted from the gel.

Example 5

The absorbtion capacity for two samples, labelled "Sample A" and "Sample B" was measured with the "liquid uptake capacity" method. The xero-gels used in both samples were prepared in the same way, with a CMCNa/HEC ratio of 3:1 and at a DVS-concentration of 0.04 mol/l. The gels were dried using acetone.

As reference, the absorption capacity for two commonly used polyacrylate-based superabsorbents was measured using the same method. The superabsorbents were SAN-WET IM5000 and IM7100 from Hoechst AG in Frankfurt, Germany.

Table 1 shows the amount of liquid absorbed by the different superabsorbent materials measured in grams/gram superabsorbent material (SAM).

TABLE 1

| SAM | Absorption capacity [g/g] |
|---|---|
| Sample A | 18.09 |
| Sample B | 22.18 |
| IM5000 | 30.58 |
| IM7100 | 28.35 |

The results which were obtained show that an acetone-dried superabsorbent material in accordance with the invention performs on a level which is almost in parity with the performance of polyacrylate-based superabsorbent materials.

DESCRIPTION OF FIGURES

The diaper 1 shown in FIGS. 1 and 2 includes a liquid-permeable covering sheet 2 and a liquid-impermeable covering sheet 3, which together enclose an absorption body 4.

Figure 1:
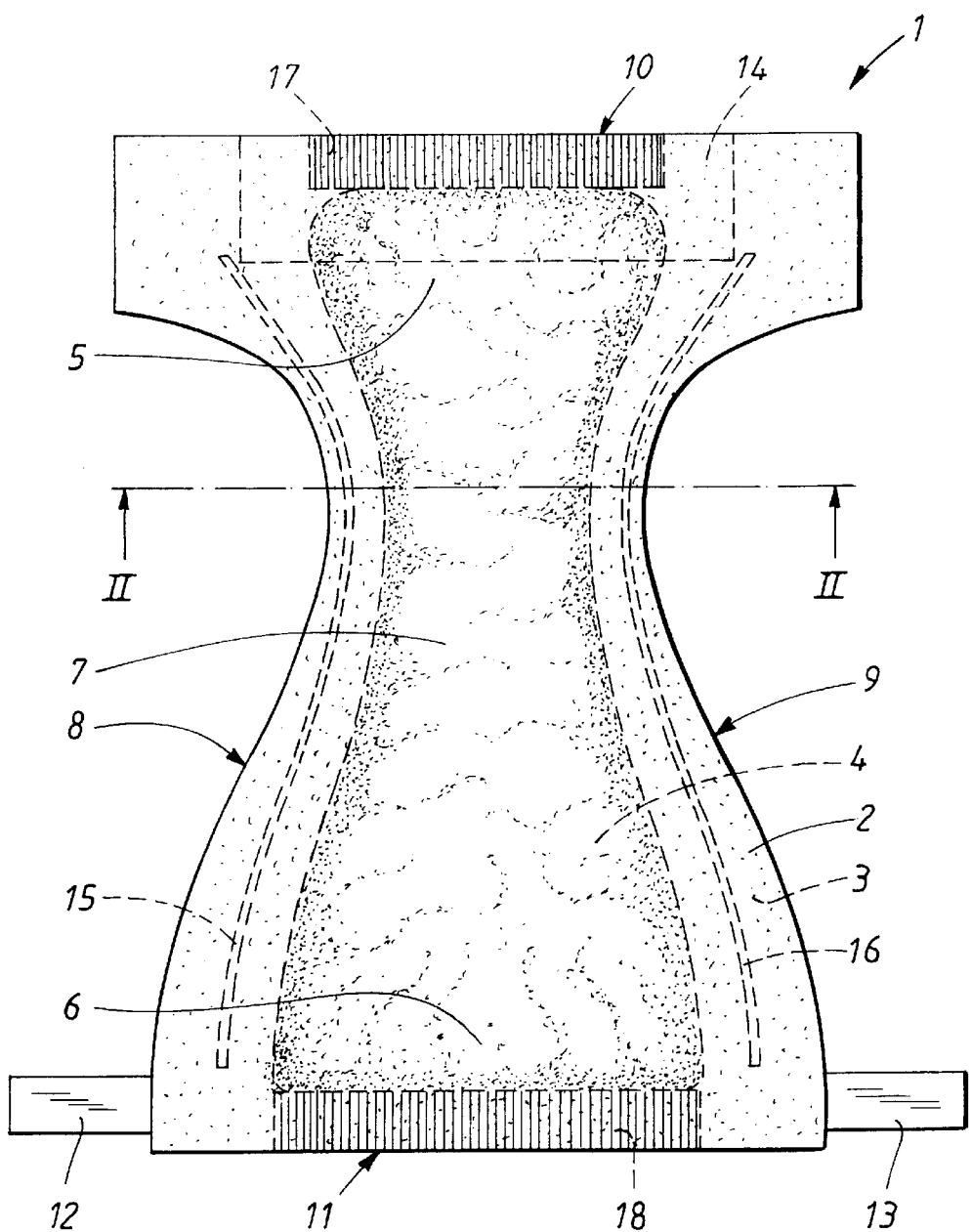
In FIG. 1, the diaper 1 is shown from the side which during use is intended to be facing a user's body, i.e. with the liquid-permeable covering sheet 2 facing the viewer of FIG. 1.

The diaper 1 has generally elongated shape, with broader front and rear portions 5,6 and a more narrow crotch portion 7. The front portion 5 is the part of the diaper which is intended to be applied toward the front of the user when the diaper is being used and the rear portion 6 is the part of the diaper which is applied to the rear on the user. In addition, the diaper 1 has two longitudinally extending, inwardly curved side edges 8,9, a front edge 10 and a rear edge 11.

The diaper 1 is of a kind which, when being used, is fastened together, thereby enclosing the lower part of the user's body in a pants-like manner. For this purpose, a tape tab 12,13 is arranged at and protruding from each side edge 8,9 in the vicinity of the rear edge 11 of the diaper. The tape tabs 12,13 are designed to cooperate with a landing area 14 arranged on the liquid-impermeable covering sheet 3 on the front portion 5 of the diaper 1. Preferably, the landing area 14 comprises some kind of reinforcement, such as, for example, an additional plastic sheet or a coating applied to the liquid-impermeable covering sheet 3. Naturally, alternative types of diaper fastening means may be used, such as buttons and buttonholes, hooks and eyes, press studs, hook and loop closures, or the like.

Furthermore, the diaper 1 is provided with longitudinally extending, elastic elements 15,16 arranged with pretention along the side edges 8,9. The elastic elements 15,16 shape the diaper 1 and serve as leg elastics during use. This means that the elastic elements 15,16 keep the side edges 8,9 of the diaper in contact with the legs of the user during use, and prevent the formation of gaps between the diaper and the user's body, which gaps might otherwise cause liquid to leak out of the diaper.

In a corresponding manner, elastic elements 17,18 are arranged along the front edge 10 and rear edge 11, respectively, in order to create elastic gasketing around the user's waist.

Figure 2:
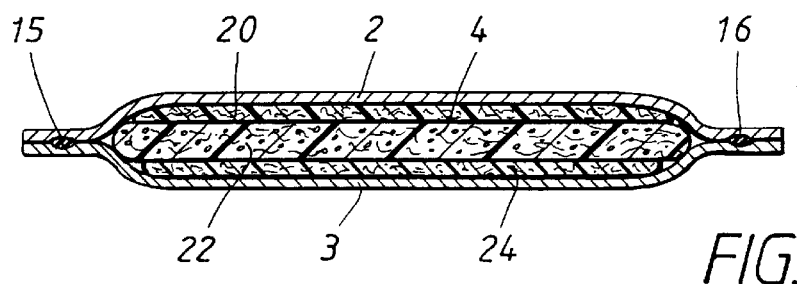

The absorption body 4 of the diaper consists in the shown embodiment, and as is best seen in FIG. 2, of a porous fluid-acquisition layer 20 arranged immediately inside the liquid-permeable covering sheet 2, an absorption layer 22, and a wicking layer 24.

The fluid-acquisition layer 20 preferably consists of a fibrous web or a comparatively thick, bulky, nonwoven material exhibiting high resilience in both wet and dry condition. In this manner, a rapid intake of liquid to the absorption layer 22 on the inside of the acquisition layer 20 is ensured, and at the same time the acquisition layer 20 serves as a distancing means and keeps body fluid, which has already been absorbed, away from the user's skin. Preferred materials for use in a fluid-acquisition layer comprise fibres which do not collapse upon wetting. Some examples of such fibres are stiffened cellulosic fibres and synthetic fibres such as polyethylene fibres, polypropylene fibres, polyester fibres, or the like.

The absorption layer 22 consists of an absorbent structure in accordance with the invention. Accordingly, the absorption layer 22 comprises highly absorbent material produced by drying a crosslinked polysaccharide-based gel with a polar solvent, for example isopropanol, ethanol, or acetone. The highly absorbent material exists in the form of particles which are mixed with fibres. A preferred fibrous material is fluffed cellulosic pulp produced according to a chemical or chemi-thermo-mechanical process. In order to enhance the integrity of the absorption layer 22, it may additionally comprise longer fibres made, for instance, from rayon, polypropylene, flax, or the like, and/or thermoplastic binding fibres or particles. The absorbent structure in the absorption layer 22 may further be bonded with a solvent-based binding agent, by needling, calendering, or in some other way.

A wicking layer 24 is arranged between the liquid-impermeable covering sheet 3 and the absorption layer 22. The wicking layer 24 is preferably a heavily compressed hydrophilic fibrous layer having thin capillaries. A material which has been found to be particularly suitable for this purpose is disclosed in WO 94/10953 and WO 94/10956. A material of this kind exists in the form of dry defibrated fibrous layers having a high density. The fibrous layers are used directly in an absorbent article without preceding defibration. The fibrous material exhibit very good absorption capacity and wicking capability.

The invention is not restricted to the hereindescribed embodiment. Hence, it is not necessary that the absorption body in an absorbent article in accordance with the invention comprises all the layers which have been described above. For instance, absorbent articles wherein all of the absorbent body consists of an absorbent structure in accordance with the invention are conceivable. Furthermore, it is possible to use absorbent bodies comprising additional or completely different components. Some examples of such components are shaping elements, nonwoven layers, tissue layers, foam in layer form or as three-dimensionally shaped bodies, odour- and bacteria-inhibiting agents, or the like.

The highly absorbent material may, as in the described example, be mixed with fluffed cellulosic pulp, or other fibres, or fibre mixtures. Alternatively, or in combination with such a described absorbent structure, the highly absorbent material may be arranged in an absorbent article in the form of a layer. The absorbent material may then either be attached to or in a substrate, such as a nonwoven material, a tissue layer, or be loosely arranged between two other layers in the absorbent structure, or in special pockets or containers in the structure.

In addition, the absorbent structure may consist of a laminate of two or more nonwoven layers or tissue layers having highly absorbent material arranged between the layers. One way to ensure that the highly absorbent material remains in such a laminate is to bind the layers together in a binding pattern. It is also possible to mechanically deform the layers, for instance by embossing, so that the highly absorbent material is locked between the layers.

Another advantageous feature of an absorbent structure in accordance with the invention is that it exhibits surprisingly high absorbency under load (AUL). Accordingly, the AUL for an absorbent structure comprising a polysaccharide-based superabsorbent material which has been dried using a polar solvent can be compared to the AUL of IM5000 and other polyacrylate-based conventional superabsorbents. Previously known polysaccharide-based superabsorbent materials have shown considerably lower AUL, in the order of about half the amount of liquid which is absorbed by IM500 or a superabsorbent in accordance with the invention.

The invention shall not be regarded as being restricted to the examples which have been described herein. Instead, a number of further embodiments are conceivable within the scope of the appended claims.

What is claimed is:

1. An absorbent structure comprising a polysaccharide based highly absorbent material, the highly absorbent material being produced by crosslinking and desiccation of a liquid solution containing a starting material in the form of a crosslinkable polysaccharide-based polymer, wherein the highly absorbent material is produced from a polymer blend comprising an electrically charged polysaccharide-based polymer and an electrically uncharged polysaccharide-based polymer and in that the starting material, after the crosslinking reaction, exists in the form of a liquid-swollen gel, and that the crosslinked, liquid-swollen gel has been desiccated by extraction with a polar solvent.

2. The absorbent structure according to claim 1, wherein the gel has been desiccated with ethanol, acetone or isopropanol.

3. The absorbent structure according to claim 1, wherein the ratio between the charged polymer and the uncharged polymer is between 2:1 and 4:1.

4. The absorbent structure according to claim 1, wherein the starting material is a mixture of carboxymethyl cellulose (CMC) and hydroxyethyl cellulose (HEC).

5. The absorbent structure according to claim 1, wherein the starting material comprises pectin.

6. The absorbent structure according to claim 1, wherein the absorbent structure comprises a three-dimensional fibrous network, and the highly absorbent material is substantially evenly distributed in the fibrous network.

7. The absorbent structure according to claim 1, wherein the highly absorbent material is arranged in a layer in the absorbent structure.

8. An absorbent article comprising an absorbent body enclosed in a casing which is at least partially liquid pervious, wherein the absorbent body comprises an absorbent structure including a highly absorbent absorption material which has been produced from a crosslinkable polymer blend comprising an electrically charged polysaccharide-based polymer and an electrically uncharged polysaccharide-based polymer and by crosslinking and drying of a liquid solution containing the polymer blend, wherein the polymer blend, after crosslinking, exists in the form of a liquid-swollen gel, and that the crosslinked, liquid-swollen gel is dried by extraction with a polar solvent.

9. The absorbent structure of claim 1, wherein the absorbent structure is a component of an absorbent article, the absorbent article being one of a diaper, an incontinence guard, a pant diaper, and a sanitary napkin.

10. The absorbent structure according to claim 3, wherein the ratio between the charged polymer and the uncharged polymer is 3:1.

11. The absorbent structure of claim 8, wherein the absorbent structure is a component of an absorbent article, the absorbent article being one of a diaper, an incontinence guard, a pant diaper, and a sanitary napkin.

* * * * *